United States Patent [19]

Suzuki et al.

[11] Patent Number: 4,981,801
[45] Date of Patent: Jan. 1, 1991

[54] AUTOMATIC CYCLING REACTION APPARATUS AND AUTOMATIC ANALYZING APPARATUS USING THE SAME

[75] Inventors: Yoshiyuki Suzuki, Tokyo; Takahiko Kato, Chigasaki, both of Japan

[73] Assignee: University of Tokyo, Tokyo, Japan

[21] Appl. No.: 734,215

[22] Filed: May 15, 1985

[30] Foreign Application Priority Data

May 15, 1984 [JP] Japan .................................. 59-97341

[51] Int. Cl.$^5$ ............................................. C12M 1/38
[52] U.S. Cl. ..................................... 435/290; 435/291; 422/64; 422/67
[58] Field of Search .................. 435/289, 290, 291; 422/52, 64, 67

[56] References Cited

U.S. PATENT DOCUMENTS

| | | | |
|---|---|---|---|
| 2,768,879 | 10/1956 | Hewson | 23/253 |
| 3,192,968 | 7/1965 | Baruch et al. | 422/64 |
| 3,549,330 | 12/1970 | Jungner et al. | 23/259 |
| 3,926,737 | 12/1975 | Wilson et al. | 435/289 |
| 4,271,123 | 6/1981 | Curry et al. | 422/67 |
| 4,298,571 | 11/1981 | DiFulvio et al. | 422/64 |
| 4,424,559 | 1/1984 | Lorincz et al. | 435/290 |
| 4,483,823 | 11/1984 | Umetsu et al. | 422/64 |
| 4,499,052 | 2/1985 | Fulwyler | 422/52 |
| 4,543,238 | 9/1985 | Mimura et al. | 422/64 |

FOREIGN PATENT DOCUMENTS

| | | |
|---|---|---|
| 1806585 | 5/1970 | Fed. Rep. of Germany . |
| 2522031 | 11/1976 | Fed. Rep. of Germany . |
| 2314491 | 7/1977 | France . |
| 78948 | 5/1983 | Japan .................................. 422/64 |

OTHER PUBLICATIONS

Analytical Chemistry, vol. 42, No. 6, May 1970, pp. 579-585 U.S.; E. W. Owen: "Sensitive, Wide-Range, Temperature Controlled Cell".

Primary Examiner—Noah P. Kamen
Attorney, Agent, or Firm—Sughrue, Mion, Zinn, Macpeak & Seas

[57] ABSTRACT

An apparatus for carrying out an enzymatic cycling reaction including a turntable arranged in a reaction tank, a number of reaction vessels being arranged in the turntable along its periphery, a device for circulating an antifreeze liquid through the reaction tank, a heater for heating the antifreeze liquid, a refrigerator for cooling the antifreeze liquid and a switching valve for selectively passing the antifreeze liquid through the heater or refrigerator. Until all the samples and cycling mixture are delivered into the reaction vessels, the reaction tank is held at a very low temperature at which no enzymatic cycling reaction proceeds. Then the antifreeze liquid is heated to an enzymatic cycling reaction temperature so as to perform the enzymatic cycling reaction simultaneously for liquids contained in all the reaction vessels for a desired period. Then, the antifreeze liquid is heated to a high temperature so as to stop simultaneously the cycling reaction in all the reaction vessels.

6 Claims, 10 Drawing Sheets

FIG_4

FIG_5

FIG_7

FIG_8

AUTOMATIC CYCLING REACTION APPARATUS AND AUTOMATIC ANALYZING APPARATUS USING THE SAME

| Name | Multiplying substrate (coenzyme) | | Cycling reaction enzyme | Excess substrate | Multiplied product | | Maximum multiplying rate per hour |
|---|---|---|---|---|---|---|---|
| NAD cycling | $NAD^+$ | NADH | alcohol dehydrogenase<br>malate dehydrogenase | ethanol<br>oxalacetate | acetaldehyde | malate* | 60,000 |
| NADP cycling | $NADP^+$ | NADPH | glucose-6-P-hydrogenase<br>glutamate dehydrogenase | glucose-6-P<br>α-ketoglutarate | 6-P-gluconate* | glutamate | 20,000 |
| CoA cycling | CoASH | acetyl-CoA | phosphotransacetylase<br>citrate synthase | acetyl-P<br>oxalacetate | phosphate | citrate* | 37,500 |

Substances marked by * are reacted with an indicator and then produced fluorescent substances such as NADH and NADPH are measured.

(1) malate + $NAD^+$ $\xrightarrow{\text{malate dehydrogenase}}$ oxalacetate + NADH + $H^+$ (2) 6-P-gluconate + $NADP^+$ $\xrightarrow{\text{6-P-gluconate dehydrogenase}}$ riblose-5-P + NADPH + $H^+$ (3) citrate $\xrightarrow{\text{aconitase}}$ cis-aconitate $\xrightarrow{\text{aconitase}}$ isocitrate, isocitrate + $NADP^+$ $\xrightarrow[\text{isocitrate dehydrogenase}]{\text{aconitase}}$ α-ketoglutarate + $CO_2$ + NADPH + $H^+$

Background of the Invention

The present invention relates generally to an enzymatic cycling technique for analyzing a small or extremely small amount of a substance contained in a sample and more particularly to an automatic enzymatic cycling reaction apparatus and an automatic analyzing apparatus for automatically analyzing a very small or extremely small amount of a substance in a sample with the aid of the automatic enzymatic cycling reaction apparatus.

For instance, in the field of biochemistry, a small amount of a substance contained in a sample is usually detected by a radio isotope method in which the substance to be analyzed is marked by a radio isotope and then is detected by a scintillation counter, a mass spectrometric method in which a substance is labeled with a stable isotope and is detected by a mass spectrometer and an immunological method in which a substance is analyzed by utilizing antigen-antibody reaction for labeled substance.

In the radio isotopic method, since the radio isotope is used, it is necessary to provide an apparatus which satisfies the safety standards for the isotope and further in order to avoid the radioactive contamination the treatment of wasted materials is very cumbersome. Further, the operation might be subjected to the radioactivity. In the mass spectrometric method using the stable isotope, since substances which can be marked with the stable isotopes are limited, the number of items to be tested is small. Further, since use is made of a mass spectrometer, it is very cumbersome to evaporate the marked substance. In the immunological method, there are a radio immuno assay using radio isotope markers, an enzyme immuno assay using enzyme markers, and a fluoroimmuno assay using fluorescent markers. In these methods it is necessary to mark antibody or antigen effecting the antigen-antibody reaction. In the radio immuno assay the same problems as those in the radio isotope method occur.

Recently, there has been proposed an enzymatic cycling method by means of which a very small amount of a substance in a sample can be analyzed without causing the above mentioned problems of the radioactive contamination, the restriction of the number of test items, etc. In the enzymatic cycling method, a substance is measured in a multiplying manner by combining two enzyme reactions. Nowadays, the following three kinds of cycling reactions have been performed as routine work.

Now the principle of the cycling reaction will be explained with reference to typical AND cycling. In the AND cycling, malate and acetaldehyde are produced in a multiplying manner by the following reaction.

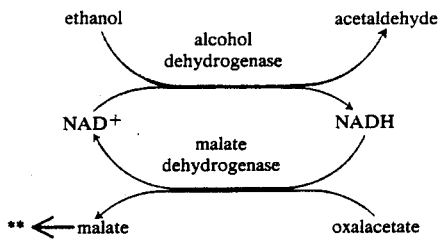

**malate is measured by a fluorometer after adding an indicator reagent.

At first, to a mixture of excess amounts of ethanol and oxalacetate are added two kinds of enzymes, i.e. alcohol dehydrogenase and malate dehydrogenase of given concentrations to form a cycling mixture. To the cycling mixture thus formed is added a very small amount of $NAD^+$ (nicotiramide adenine dinucleotide oxidation type) which is a kind of a coenzyme.

Then one molecule of $NAD^+$ is reduced by the catalytic action of the alcohol dehydrogenase using the ethanol as substrate to produce one molecule of acetaldehyde and one molecule of NADH. Then, one molecule of NADH thus produced is oxidized by the catalytic action of the malate dehydrogenase using the oxalacetate as substrate to produce one molecule of $NAD^+$ and one molecule of malate. Therefore, when the cycle reaction is repeated by 1,000 times, there are produced 1,000 molecules of acetaldehyde and malate although the initial liquid contains only one molecule of $NAD^{30}$.

To the mixture containing the acetaldehyde and malate produced in the multiplying mode are added an excess amount of $NAD^+$ and a given amount of malate dehydrogenase to effect the following indicator reaction.

malate + $NAD^+$ $\xrightarrow{\text{malate dehydrogenase}}$ oxalacetate + NADH + H⁺

In this manner, the accumulated or multiplied malate is transferred quantitatively into fluorescent NADH. Therefore, by measuring the intensity of fluorescent light emitted from the excited NADH, it is possible to measure a very small amount of NAD⁺ in a sample with the aid of a calibration curve relating the fluorescent light intensity to the concentration of NAD⁺. In the NAD cycling, NADH is simultaneously produced in the multiplying manner. Therefore, NADH may be measured in the same manner as that explained above.

In the NADP cycling and CoA cycling, the multiplying reaction is carried out in the similar manner to that explained above.

By means of the enzymatic cycling method, it is also possible to measure substances which can be transferred into the multiplying substrate such as NAD⁺, NADH, NADP and CoA. For instance, a very small amount of ethanol contained in a blood serum may be measured in the following manner. At first, the ethanol in the serum sample is transferred quantitatively into NADH under the existence of an excess amount of NAD⁺ in accordance with the following transfer reaction, while alcohol dehydrogenase is used as a catalyst.

ethanol + NAD⁺ $\xrightarrow{\text{alcohol dehydrogenase}}$ acetaldehyde + NADH + H⁺

Next, the solution is heated to, for instance 70° C., while a pH value of the solution is adjusted to 11 to 12. During this treatment, NAD⁺ remained in the solution is destroyed. Then, the above explained NAD cycling reaction is carried out, while NADH remained in the solution is used as multiplying substrate. In this manner, a very small amount of ethanol may be measured accurately by the enzymatic cycling method.

Most of substances of living bodies or substances produced by enzyme reactions in the living bodies may be transferred into multiplying substrates in the cycling reactions, and therefore the enzymatic cycling method is very effective for measuring various substances by utilizing specificities of various enzymatic reactions.

Nowadays the enzymatic cycling method has been used to analyze various substances such as glucides and their intermediary metabolites, amino acids and their relating substances, some kinds of lipids (glucide phospholipid) and substances relating to nucleotide, and to effect the enzyme assay for various kinds of enzymes relating to metabolism. For instance, in case of analyzing an amniotic fluid extracted from a pregnant woman, it is possible to diagnose congenital metabolisms of fetus such as Krabbe's disease, galactosemia, $G_{MI}$-gangliosidosis and Fabry's disease.

As explained above, by utilizing the transfer reactions for transferring substances to be analyzed into the multiplying substrates (coenzymes), the enzymatic cycling method can afford the measurement of extremely small amounts of substances in the multiplying mode. Therefore, the enzymatic cycling method can be applied not only to biochemistry and medicine, but also to a broader sense biology including biochemistry, physiology and cell biology, pharmacology, agricultural chemistry and chemical analysis. In the medical field, since a sample amount is extremely small, it is possible to diagnose not only various diseases of fetus, but also various diseases of newborn and infant. Further, the enzymatic cycling method may be applied to forensic medicine and pathology. In the application to the biology, pharmacology and agricultural chemistry, since given substances may be analyzed quantitatively and qualitatively, various cells such as microorganism, cultured cell and living tissue may be analyzed one by one and thus quality of particular cells can be investigated in detail. In the field of analytical chemistry, extremely small amounts of samples in the organic chemistry may be analyzed accurately.

Heretofore, the above explained enzymatic cycling method has been carried out manually. That is to say, at first a given amount of a sample (multiplying substrate) and an aliquot of a cycling reaction enzyme and an excess amount of a substrate are poured into a reaction vessel such as a test tube. Until a given number of samples have been delivered into reaction vessels, the reaction vessels are immersed into a first thermostat which is held at a temperature such as −30° C. at which the cycling reaction does not proceed. After a given number of samples have been delivered into the reaction vessels, the reaction vessels are transferred into a second thermostat held at a temperature such as 25° C. at which the cycling reaction occurs. Times at which particular reaction vessels are transferred into the second thermostat are recorded manually. When a given cycling reaction period has been elapsed for a reaction vessel, the relevant reaction vessel is immersed for two or three minutes into a third thermostat held at a temperature such as 100° C. at which the cycling reaction is stopped due to the alternation of the enzymes. Then, the reaction vessel is transferred into a fourth thermostat held at a temperature such as 38–40° C. at which the indicator reaction takes place and an indicator reagent is delivered into the reaction vessel. After the indicator reaction has been performed for a predetermined period, the liquid contained in the reaction vessel is introduced into a fluorometer and is excited by radiation of a given wavelength to emit fluorescent light. Then the intensity of fluorescent light thus emitted is measured. It should be noted that in the CoA cycling, after the lapse of the predetermined indicator reaction period, but prior to the fluorometry a given amount of a buffer solution is delivered into the reaction vessel.

In the enzymatic cycling method, the temperature and period of the cycling reaction are important factors which determine an amount of an accumulated substance such as malate. For instance, in the NAD cycling, the following relation is generally obtained.

$$P = k_c C t$$

wherein C is a sum of concentrations of NAD⁺ and NADH, t is the reaction period, P is the concentration of accumulated malate and $k_c$ is the cycling rate. It is apparent that the amount of malate is proportional to the reaction period t. Further, the cycling rate $k_c$ is expressed as follows.

$$k_c = \frac{k_a k_b}{k_a + k_b}$$

wherein $k_a$ is a primary reaction coefficient of alcohol dehydrogenase with respect to NAD⁺ and $k_b$ is a primary reaction coefficient of malate dehydrogenase with respect to NADH. Since $k_a$ and $k_b$ are proportional to concentrations of alcohol dehydrogenase and malate dehydrogenase, respectively, the cycling rate $k_c$ is also proportional to the concentration of these enzymes. However, when the enzyme concentrations in the cycling mixture become higher, the cycling reaction does not proceed, because NAD+ and NADH are bound to the enzymes. In NAD cycling, the cycling reaction proceeds at a temperature range of 4° to 25° C., in NADP cycling the cycling reaction takes place at a temperature range of 4' to 38° C., and in CoA cycling the cycling reaction is carried out at a temperature range of 4° to 30° C. The maximum multiplying rates per hour of 60,000, 20,000 and 37,500 in these cyclings are obtained at 25° C., 38° C. and 30° C., respectively. However, when the cycling reactions are continued for more than three hours at these temperatures, the activity of enzymes is lost and thus the multiplying rates are gradually decreased. For instance, in NAD cycling the multiplying rate per hour at 4° C. is decreased to 17% of the maximum multiplying rate at 25° C., but since at 4° C. the enzymes do not loose the activity, given the cycling reaction is continued for more than three hours, for example, twenty hours, the amount of malate can be increased by 200,000. Therefore, in the cycling reaction, the reaction temperature and period are very important factors for increasing the amount of accumulated substance by any desired multiplier.

As explained above, in the enzymatic cycling, the multiplying factor of the accumulated substance is predominantly determined by the reaction temperature and period. Therefore, in the known manual method times of immersion of particular reaction vessels into the second thermostat have to be recorded accurately and after a given reaction period has elapsed, the reaction vessel has to be immediately transferred into the third thermostat held at 100° C. to stop the cycling reaction. This requires a lot of labor of an operator and might introduce inevitable human errors. Therefore, it is difficult to obtain highly accurate and reliable analytic results.

In order to avoid the above mentioned drawbacks, it has been desired to develop an apparatus for easily carrying out the enzymatic cycling method. In such an apparatus, it is necessary to control the cycling reaction liquids contained in the reaction vessels at various temperatures and further the reaction temperature and/or period has to be varied in order to obtain a desired multiplying rate. It is considered that a conventional biochemical analyzer is altered so as to carry out the enzymatic cycling. The conventional analyzer comprises only one thermostat usually held at 37° C. and reaction vessels are successively fed through the thermostat at a given pitch. Therefore, by merely making the feeding pitch variable and providing a plurality of thermostats held at different temperatures, there might occur various problems, because in the enzymatic cycling the multiplying rate has to be varied over a very wide range. Due to the above reason, there have not been proposed an automatic cycling reaction apparatus which can perform automatically the enzymatic cycling method in a simple and reliable manner and an automatic analyzing apparatus utilizing the enzymatic cycling reaction.

SUMMARY OF THE INVENTION

The present invention has for its object to provide an automatic cycling reaction apparatus in which an enzymatic cycling reaction can be carried out automatically in a simple and precise manner.

It is another object of the invention to provide an automatic cycling reaction apparatus in which the amplifying rate, i e. the cycling rate can be easily adjusted over a wide range.

It is still another object of the invention to provide an automatic analyzing apparatus in which an extremely small amount of a substance can be measured in a highly accurate and reliable manner by using the enzymatic cycling reaction.

According to the invention, an automatic cycling reaction apparatus comprises first means for supporting a plurality of reaction vessels each containing given amounts of a sample and a cycling mixture including enzymes; and second means for holding simultaneously liquids contained in all the reaction vessels at a given cycling reaction temperature for a given period, holding all the liquids simultaneously at a first temperature at which a cycling reaction is stopped due to loss of activity of enzymes, and then keeping all the liquids simultaneously at a second temperature lower than the first temperature.

DESCRIPTION OF THE PREFERRED EMBODIMENTS

Figure 1:
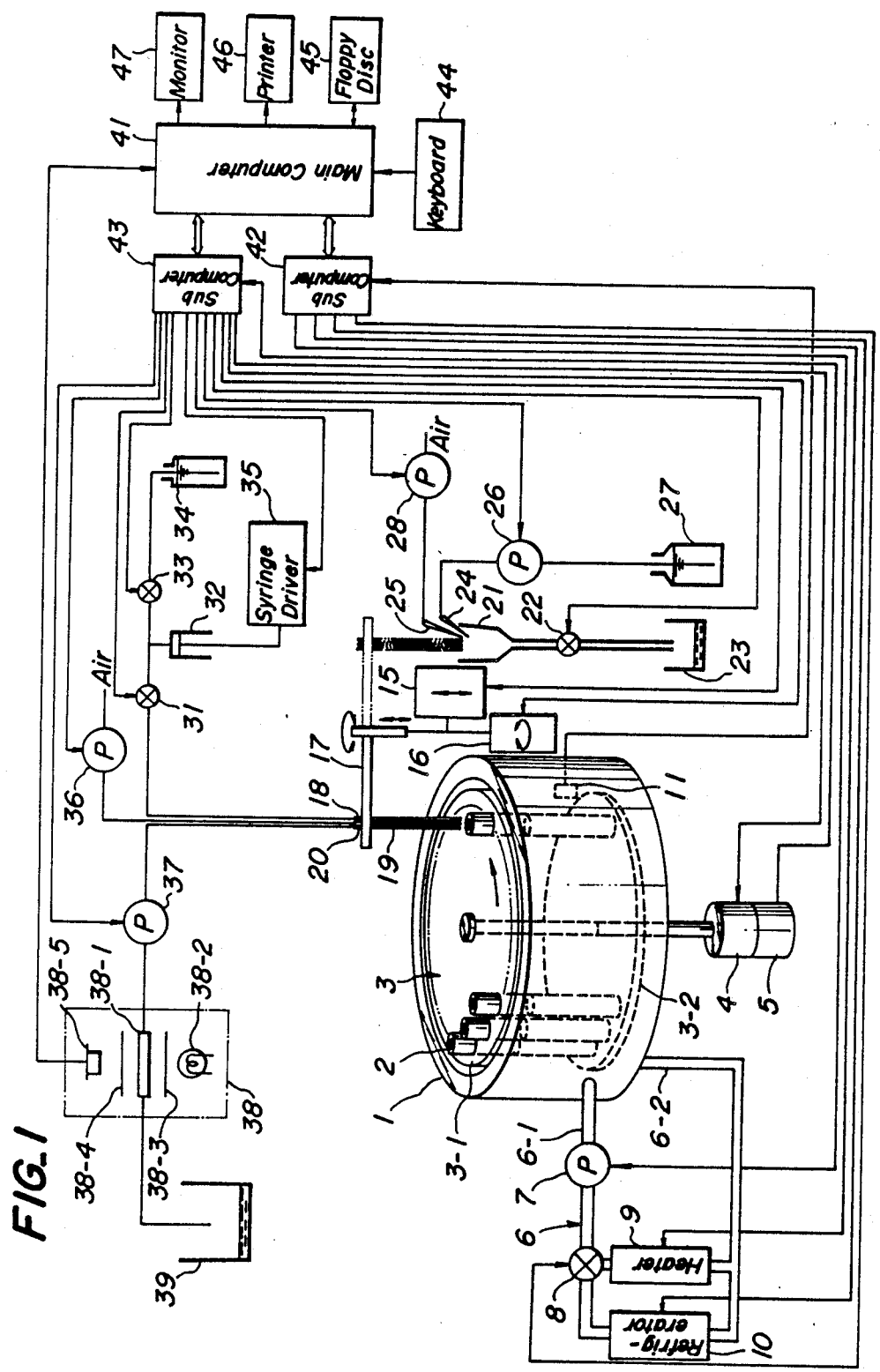
FIG. 1 is a schematic view showing an embodiment of the automatic analyzing apparatus according to the invention.

FIG. 1 is a schematic view showing an embodiment of the automatic analyzing apparatus according to the invention. In the present embodiment, the apparatus comprises only one reaction tank 1 in which a plurality of reaction vessels 2 are contained. A thermostatic medium of the reaction tank 1 is controlled to have various temperatures so as to keep simultaneously a plurality of liquids in the reaction vessels at given temperatures. In the reaction tank 1 is rotatably arranged a turntable 3 which can hold removably a hundred reaction vessels 2 in the form of test tube arranged equidistantly along a periphery thereof. The turntable 3 comprises an upper disc 3-1 and a lower disc 3-2, these discs being coupled with a driving shaft of a motor 4. In the upper disc 3-1 there are formed a hundred holes through which the reaction vessels are inserted until their bottoms are brought into contact with the lower disc 3-2. The rotational angle of the driving shaft of motor 4 is detected by a rotary encoder 5. Under the control of the detected rotational angle, the turntable 3 is rotated in a stepwise manner in a direction shown by an arrow at a pitch equal to a pitch of the array of holes formed in the upper disc 3-1. The reaction tank 1 is filled with a thermostatic medium such as an antifreeze liquid which is circulated through the reaction tank by means of pipe 6, circulating pump 7, switching valve 8, heater 9 or refrigerator 10. The pipe 6 is covered with heat insulating material and its inlet 6-1 is connected to a side wall of the reaction tank 1 and its outlet 6-2 is coupled with a bottom of the tank so that the thermostatic fluid can circulate effectively within the reaction tank 1. Further, inside the reaction tank 1 is arranged a temperature sensor 11 for detecting a temperature of the antifreeze liquid. It should be noted that the antifreeze liquid is contained in the reaction tank 1 to such a level that portions of reaction vessels containing liquids are sufficiently immersed in the antifreeze liquid.

Besides the reaction tank 1 is arranged an arm 17 which is moved up and down by a mechanism 15 as well as is rotated by a rotating mechanism 16. To a front end of the arm 17 are secured three nozzles 18, 19 and 20 which may be inserted into a reaction vessel indexed at a liquid delivery position.

At a position outside the reaction tank 1 there is further arranged a washing tank 21. By rotating the arm 17 above the washing tank 21 and then descending the arm, it is possible to immerse the nozzles 18 to 20 into the washing tank 21. The washing tank 21 is connected to a waste liquid tank 23 via a valve 22. Above the washing tank 21 are arranged two nozzles 24 and 25, the nozzle 24 being communicated with a washing liquid tank 27 by means of a pump 26 so as to eject a washing liquid into the washing tank 21. The other nozzle 25 is coupled with an air pump 28 to jet an air stream.

The nozzle 18 secured to the arm 17 communicates with an indicator reagent tank 34 via valve 31, delivery syringe 32 and valve 33. By driving the valves 31, 32 and a syringe driving mechanism 35, it is possible to deliver a given amount of an indicator reagent into a reaction vessel 2. It should be noted that a conduit extending from the indicator reagent tank 34 to a tip of the nozzle 18 is always filled with the indicator reagent. The nozzle 19 is coupled with an air pump 36 so as to eject an air stream from the nozzle tip. Further, the nozzle 20 is extended to a waste liquid tank 39 by means of a pump 37 and a fluorometer 38 to supply a reaction liquid in a reaction vessel 2 into the fluorometer 38 after the indicator reaction. The fluorometer 38 comprises a flowcell 38-1 in which the reaction liquid is introduced, a light source 38-2, a filter 38-3 for projecting a light flux having a given wavelength into the flowcell, a filter 38-4 for transmitting fluorescent light and a photoelectric detector 38-5 for detecting the fluorescent light.

In the present embodiment, in order to control the operation of various units, there are arranged a main computer 41 and two sub computers 42 and 43 connected to the main computer 41. Under the command from the main computer 41, the sub computer 42 controls the temperature of the thermostatic medium, i.e. antifreeze liquid in the reaction tank 1 and the sub computer 43 controls the rotational movement of the turntable 3 and other various movements related thereto. To this end, the output of the temperature sensor 11 is supplied to the sub computer 42 and then the sub computer 42 controls the circulating pump 7, switching valve 8, heater 9 and refrigerator 10. The output of the rotary encoder 5 is supplied to the sub computer 43 which then controls the motor 5, up and down mechanism 15 and rotating mechanism 16 for the arm 17, valve 22, pump 26, air pump 28, valves 31, 33, syringe driving mechanism 35, air pump 36 and pump 37. The output of the photoelectric detector 38-5 of the fluorometer 38 is supplied to the main computer 41 and the main computer 41 performs given calculations on the basis of the received output to identify and measure a kind and an amount of a substance to be analyzed. To the main computer 42 are connected a keyboard 44 for entering various kinds of information, a floppy disc device 45 for storing the entered information relating to the analytic operation and for reading out the stored information, a printer 46 for printing out analytic results and a monitor 47 for displaying various kinds of information such as the entered information and analytic results.

Figure 2:
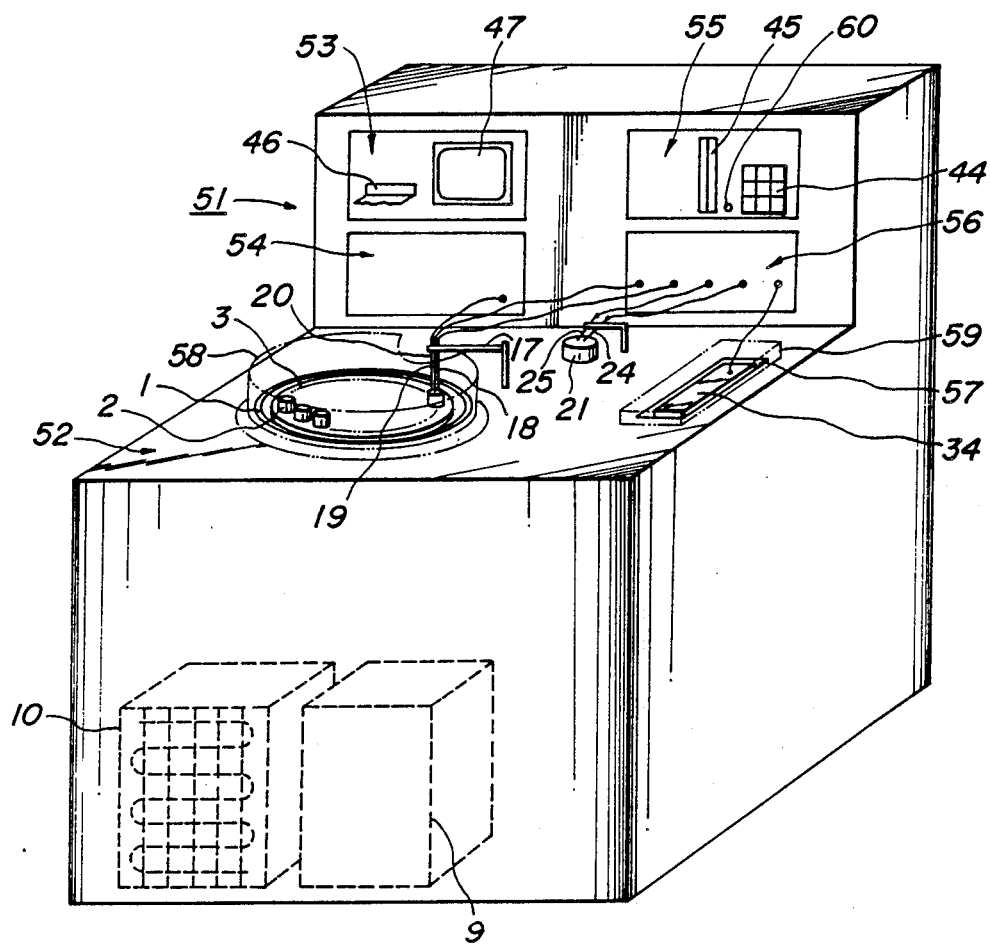
FIG. 2 is a perspective view illustrating an outer appearance of the apparatus shown in FIG. 1.

FIG. 2 is a perspective view illustrating an outer appearance of the automatic analyzing apparatus shown in FIG. 1. A main apparatus 51 comprises reaction unit 52, printing and displaying unit 53, fluorometry unit 54, control unit 55 and pump unit 56. The reaction unit 52 comprises the reaction tank 1 and its temperature controlling system, turntable 3 and its driving system, arm 17 and its driving system, washing tank 21 and thermostat 57 which is kept at 4° C. so as to prevent the indicator reagent contained in the indicator reagent tank 34 from being altered. The temperature of the thermostat 57 is controlled by the refrigerator 10 which is used to control the temperature of the reaction tank 1. It should be noted that the opening of the reaction tank 1 is covered with a removable lid 58 except for a portion through which the nozzles 18 to 20 are moved. Similarly, the thermostat 57 is covered with a removable lid 59. The printing and displaying unit 53 comprises the printer 46 and monitor 47 shown in FIG. 1, and the fluorometry unit 54 comprises the pump 37 and fluorometer 38. The control unit 55 comprises the main and sub computers 41 and 42, 43, keyboard 44, and floppy disc device 45. The control unit 55 further comprises a start button 60 for initiating the analysis. The pump unit 56 comprises the nozzle washing pump 26 and air pump 28, indicator reagent delivery valves 31, 33 and syringe 32, syringe driving mechanism 35, and air pump 36 connected to the nozzle for mixing the contents in a reaction vessel.

Now, the operation of the automatic analyzing apparatus will be explained by taking NAD cycling by way of example.

First, the circulating pump 7 is operated and the switching valve 8 is switched on the side of the refrigerator 10. Then the refrigerator 10 is controlled in an on-off manner in accordance with the output of the temperature sensor 11 so as to keep the antifreeze liquid at $-30°$ C. Then a given number of reaction vessels 2, i.e. a hundred reaction vessels each containing 1 $\mu$l of a sample and 50 $\mu$l of a cycling mixture are set on the turntable 3. This may be performed in the following manner. Prior to the delivery of samples, 50 $\mu$l of cycling mixture is delivered into all reaction vessels which are kept cold by ice, and a hundred samples which contain $NAD^+$ transferred from substance to be analyzed by means of a transfer reaction are delivered into a hundred sample cups. Then, 1 $\mu$l of each samples in respective sample cups are delivered into respective reaction vessels one by one and the reaction vessels are successively set on the turntable 3.

After a hundred reaction vessels each containing given aliquots of sample and cycling mixture have been set on the turntable 3, the reaction tank 1 is covered with the lid 58 and the start button 60 is depressed. Then the switching valve 8 is changed onto the side of the heater 9 so as to heat the antifreeze liquid. Under the control of the output of the temperature sensor 11, the switching valve 8, heater 9 and refrigerator 10 are so controlled that the temperature of the antifreeze liquid is maintained at 25° C. for one hour.

Figure 3:
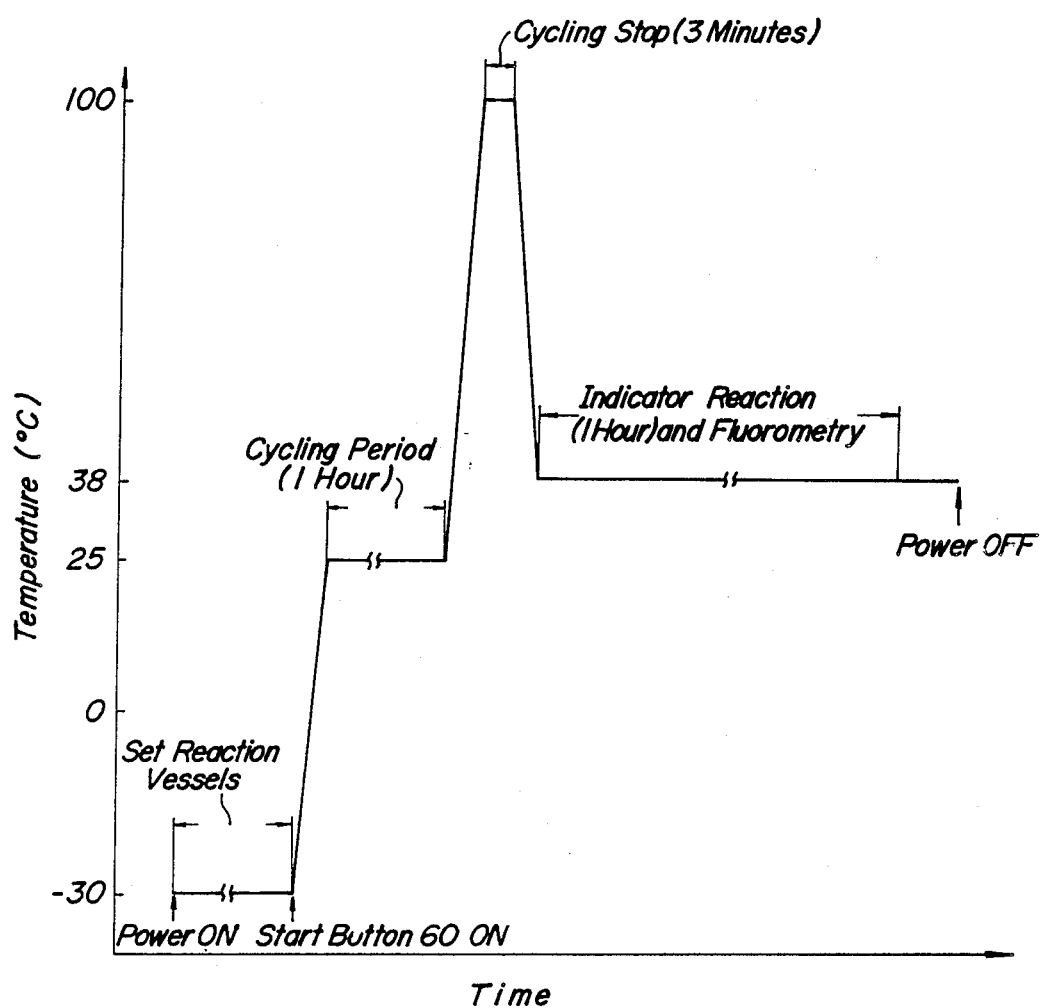
FIG. 3 is a graph showing the variation of the temperature during the analysis.

FIG. 3 is a graph showing a temperature variation of the reaction tank 1. After the cycling reaction period of one hour has elapsed, the switching valve 8 is maintained to be switched on the side of heater 9 and the antifreeze liquid is rapidly heated and the temperature of reaction tank 1 is kept at 100° C. for three minutes by controlling the valve 8, heater 9 and refrigerator 10 in accordance with the output of the temperature sensor 11. By heating the cycling reaction liquid up to 100° C., the enzymes contained in the liquid loose their activity and therefore the cycling reaction is stopped.

Then, the antifreeze liquid is cooled and the reaction tank 1 is kept at 38° C. as illustrated in FIG. 3. Then 1.0 ml of the indicator reagent is delivered into successive reaction vessels in the following manner.

The arm 17 is moved downward by means of the up and down mechanism 15 and the tips of nozzles 18 to 20 are immersed into a liquid contained in a reaction vessel which is just indexed at the delivery position. Then after the valve 31 has been closed and the valve 33 has been opened, the syringe driving mechanism 35 is operated to suck 1.0 ml of the indicator reagent into the syringe 32. Then, after the valve 31 has been opened and the valve 33 has been closed, the mechanism 35 is driven again to discharge the 1.0 ml of the indicator reagent from the nozzle 18 into the liquid contained in the reaction vessel 2. At the same time, the air pump 36 is driven to eject the air stream from the nozzle 19 into the liquid to agitate or mix the cycling reaction liquid and indicator reagent in the reaction vessel 2. Next, the arm 17 is moved upward by the up and down mechanism 15 so that the nozzles 18 to 20 are removed from the reaction vessel 2. Then the rotating mechanism 16 is driven to rotate the arm 17 into the position just above the washing tank 21, and the arm 17 is moved downward to immerse the nozzles 18 to 20 into the washing tank 21. Then the pump 26 is operated to deliver a given amount of the washing liquid contained in the tank 27 by means of the nozzle 24 into the washing tank 21. During this delivery of the washing liquid, the valve 22 is closed so that parts of nozzles 18 to 20 which have been brought into contact with the liquid in the reaction vessel are immersed into the washing liquid remained in the washing tank 21. Then the valve 22 is opened to discharge the washing liquid in the tank 21 into the waste liquid tank 23. Then the air pump 28 is driven to jet the air stream from the nozzle 25 against the nozzles 18 to 20 to remove any washing liquid adhered to the outer walls of nozzles 18 to 20. After that, the arm driving mechanisms 15 and 16 are operated to ascend and rotate the arm 17 and the nozzles 18 to 20 are indexed at the delivery position above the turntable 3. During the above indicator reagent delivery operation, the turntable 3 is rotated by one pitch in the given direction. By repeating the above operation, 1.0 ml of indicator reagent is delivered into successive reaction vessels 2. It should be noted that during the delivery of the indicator reagent, the pump 37 connected to the nozzle 20 is remained inoperative.

In each of the reaction vessels 2, the indicator reaction is carried out for one hour and then the liquids contained in successive reaction vessels 2 are introduced into the fluorometer 38 to measure the intensity of fluorescent light. For this purpose, the arm 17 is moved in the same manner as that explained for the indicator reagent delivery, and the nozzles 18 to 20 are first immersed into a liquid in a reaction vessel 2 just situating at the delivery position. Then the pump 37 is operated to introduce a given amount of the liquid (0.3 ml) from the nozzle 20 into the flowcell 38-1. Then the arm 17 is moved upward, then is rotated into the washing position above the washing tank 21, and is moved downward. During this movement the liquid introduced into the flowcell is measured and then discharged into the tank 39 by driving the pump 37. Now the nozzles 18 to 20 are washed by operating the pumps 26 and 28 in the same manner as that explained above. During the fluorometry period, the valves 31, 33 connected to the nozzle 18, syringe 32 and the air pump 36 connected to the nozzle 19 are remained inoperative. Further, in order to avoid contamination between successive liquids in the conduit coupled with the fluorometer 38, the conduit is washed by flowing the washing liquid therethrough. This may be done as follows. After the outer walls of nozzles 18 to 20 have been washed and the wasted washing liquid has been discharged into the waste liquid tank 23, the fresh washing liquid is again introduced in the washing tank 21. Then the pump 37 is driven again to flow the washing liquid through the nozzle 20 and fluorometer 38. It should be noted that the conduit connected to the fluorometer 38 may be washed by passing the air stream therethrough.

The output from the photoelectric detector 38-5 is supplied to the main computer 42 and the analytic result obtained by effecting the calculation based on the output is printed out by the printer 46 as well as displayed on the monitor 47.

After the liquids contained in all the reaction vessels 2 have been successively measured by the fluorometer 38, the operation of the apparatus is stopped. It should be noted that the turntable 3 may be always rotated intermittently at a given period, or may be rotated intermittently only during the indicator reagent delivery period and fluorometry period.

Figure 4:
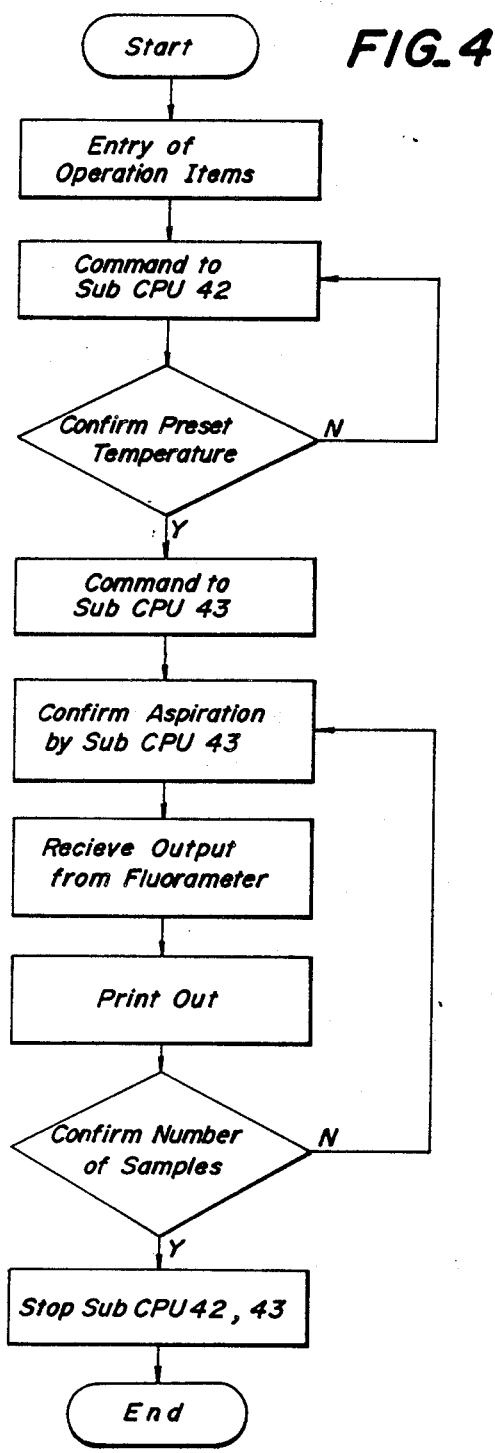
FIGS. 4, 5 and 6 are flow charts explaining the operation of the apparatus shown in FIG. 1.
Figure 5:
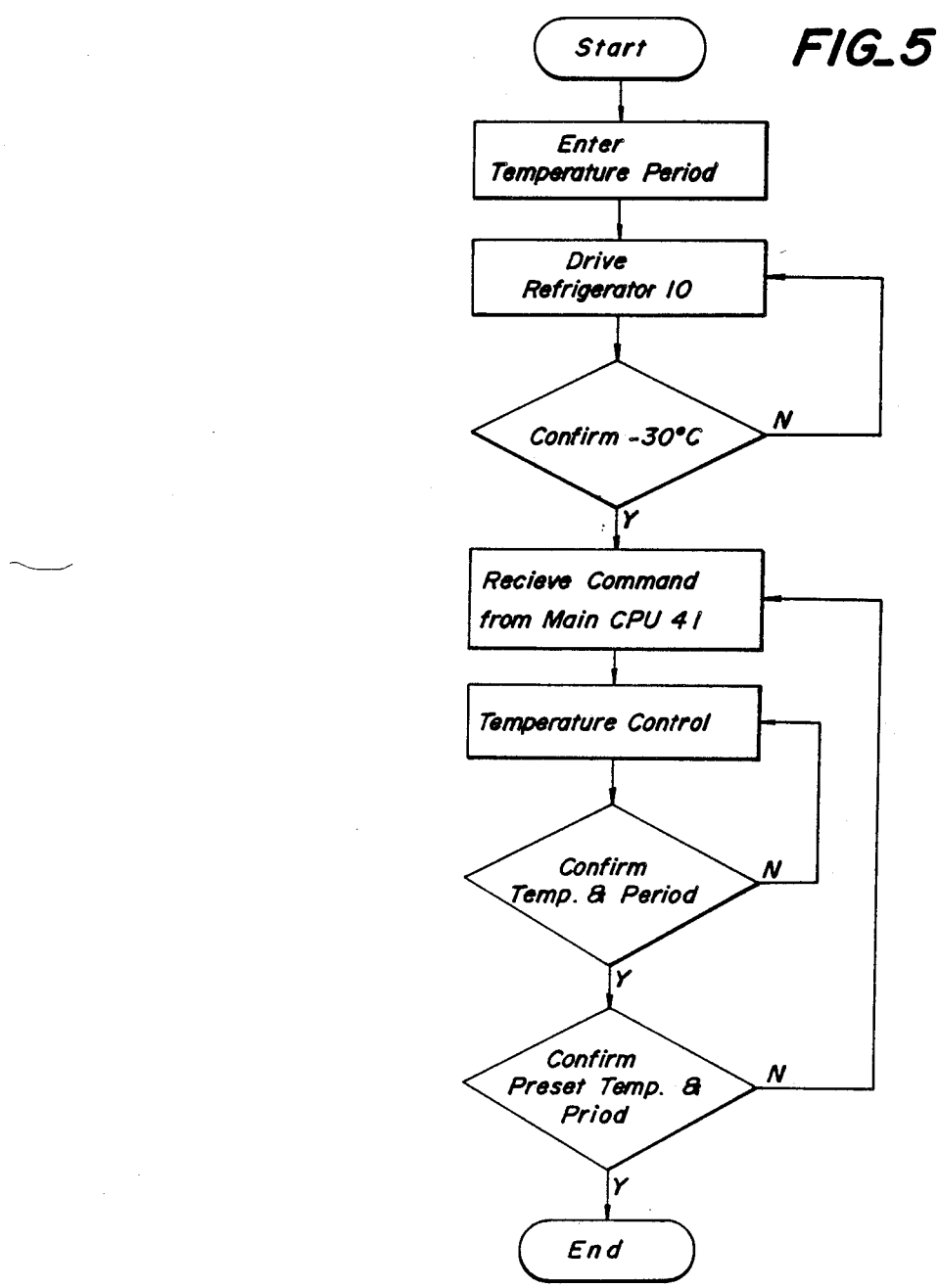
Figure 6:
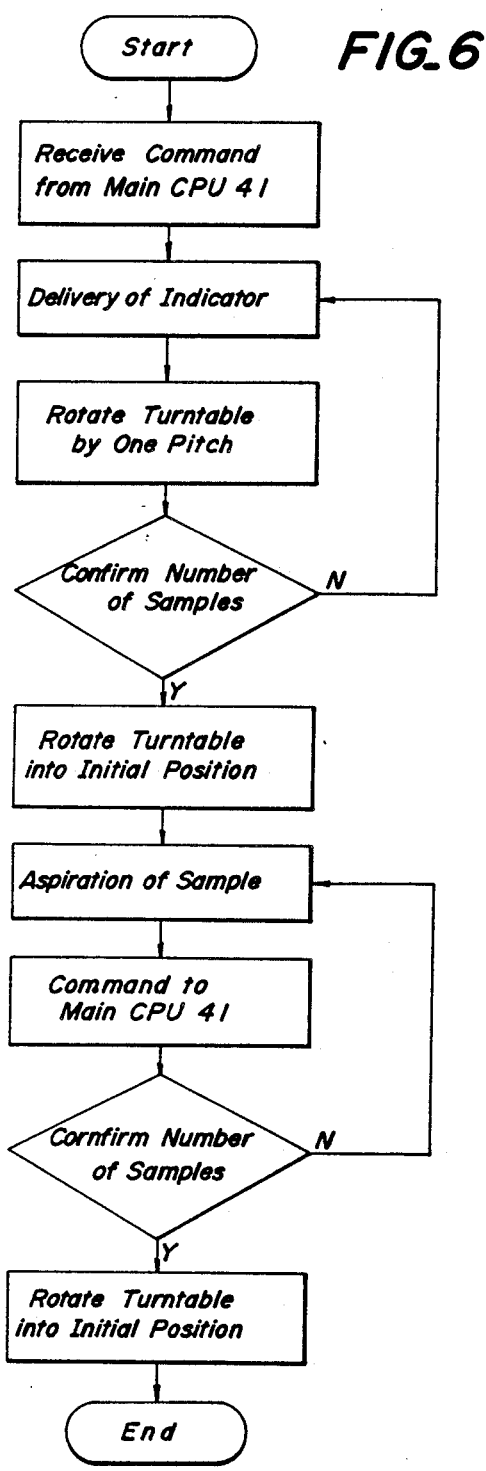

In the present embodiment, the various units are controlled by the main computer 41 via the sub computers 42 and 43 in accordance with the program recorded in the floppy disc device 45. FIGS. 4, 5 and 6 are flow charts showing the operations controlled by the main computer 41, and sub computers 42 and 43, respectively. The operations represented by the flow charts are clearly understood by those skilled in the art with reference to the previous explanation and thus will not be explained any more.

The automatic analyzing apparatus of the present embodiment may be equally applied to NADP cycling. Further, if the apparatus is applied to CoA cycling, to the arm 17 is secured one more nozzle which is connected to a buffer solution delivery mechanism similar to that indicator reagent delivery mechanism and a given amount of a buffer solution is delivered into a reaction vessel 2 after the lapse of the indicator reaction, but prior to the fluorometry. During the delivery of the buffer solution into the reaction vessel, the air stream may be ejected from the nozzle 19.

As explained above in detail, according to the automatic analyzing apparatus of the present embodiment, by utilizing the simple automatic cycling reaction apparatus in which the temperature of the thermostatic liquid circulating through the single reaction tank 1 is controlled by the heater 9 and refrigerator 10, the liquids in all the reaction vessels 2 set on the turntable 3 provided in the reaction tank can be simultaneously controlled to desired temperature for predetermined periods, and therefore the enzymatic cycling reaction can be performed highly accurately and reliably, while the apparatus can be made small in size. It should be noted that in the present embodiment there is provided the washing mechanism for cleaning the nozzles 18 to 20, but if contamination between successive liquids contained in the reaction vessels does not occur, the washing mechanism may be omitted.

Figure 7:
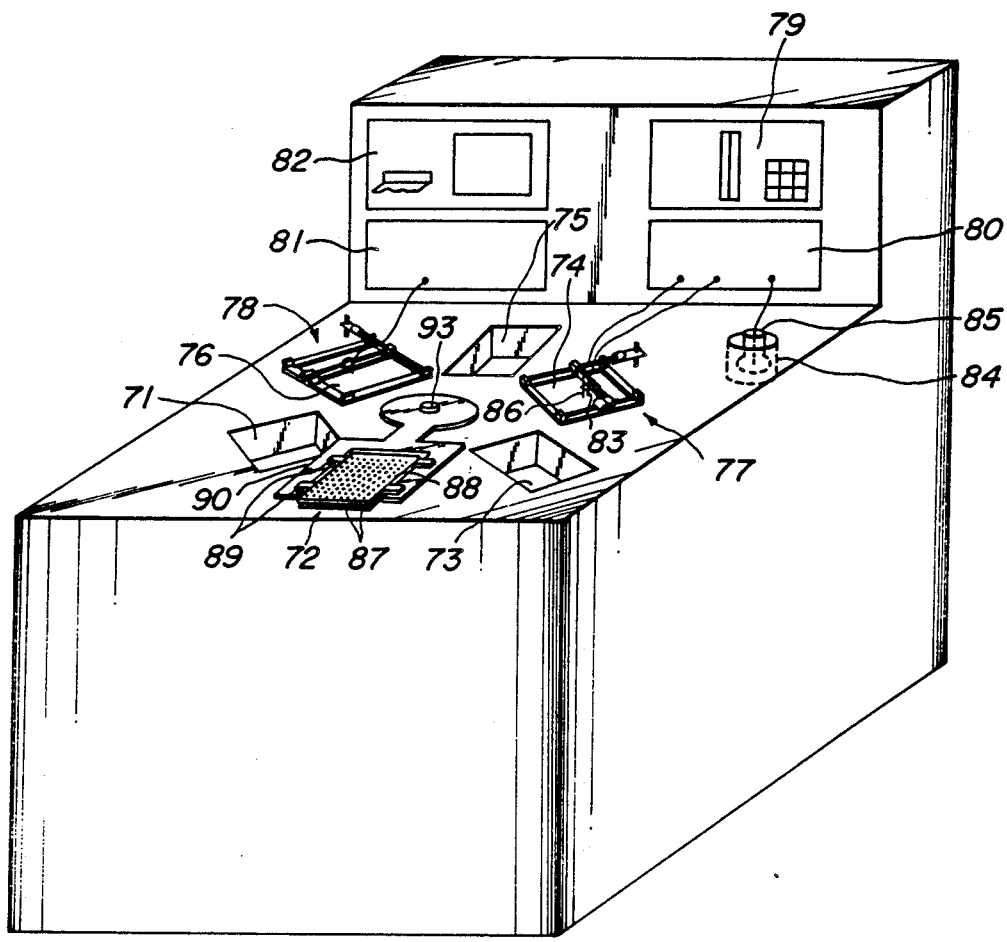
FIG. 7 is a perspective view depicting another embodiment of the automatic analyzing apparatus according to the invention.
Figure 8:
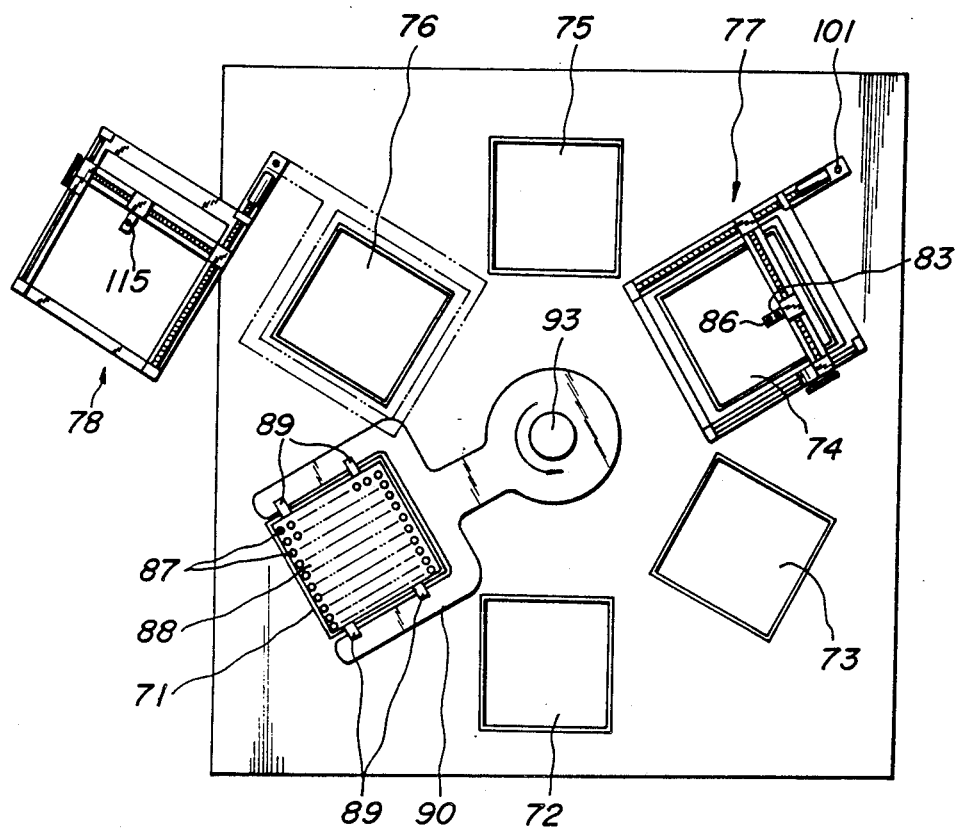
FIG. 8 is a plan view showing a reaction unit of the apparatus shown in FIG. 7.

FIG. 7 is a perspective view showing another embodiment of the automatic chemical analyzer according to the invention. In this embodiment, a main body of the analyzer is divided into a reaction unit and a process unit. In the reaction unit, five thermostats 71 to 75 and one stage 76 are arranged. The first thermostat 71 is maintained at a temperature of $-30°$ C. by using an antifreeze liquid as a thermostatic medium. Moreover, the second thermostat 72 is maintained at a cycling temperature between 4° C. and 38° C., and the third thermostat 73 is kept at a temperature of 100° C. at which the cycling reaction is stopped. Further, the fourth thermostat 74 is maintained at a temperature of 4° C. at which the indicator reaction is not started, and the fifth thermostat 75 is kept at a temperature of 38° C. at which the indicator reaction is started. Moreover, a thermostat is not provided in the stage 76 because the stage 76 is kept at a room temperature. At a position of the fourth thermostat 74 is arranged a delivery and stir device 77 of the indicator reaction liquid, and at the stage 76 is provided a suction device 78 for introducing the test liquid in the reaction vessel into a flowcell arranged in a fluorometry unit as illustrated in FIG. 8. In the process unit, control unit 79, pump unit 80, fluorometry unit 81 and printer unit 82 are arranged. The construction and function of these units are the substantially same as those of the embodiment mentioned above. For example, the pump unit 80 comprises a pump connected with a delivery nozzle 83 arranged in the delivery and stir device 77 and with a tank 85 for the indicator reagent provided in a thermostat 84 maintained at 4° C.

Figure 9:
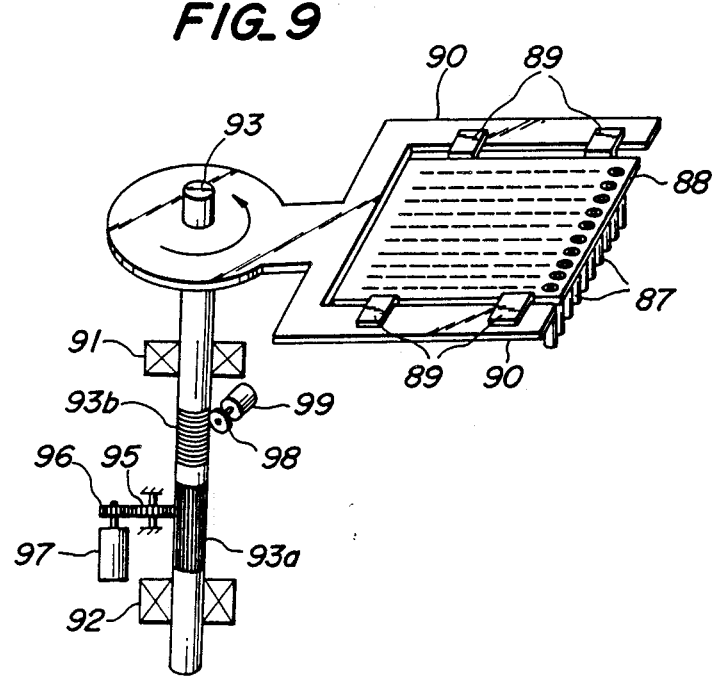
FIG. 9 is a perspective view illustrating a mechanism for driving reaction vessels.
Figure 10:
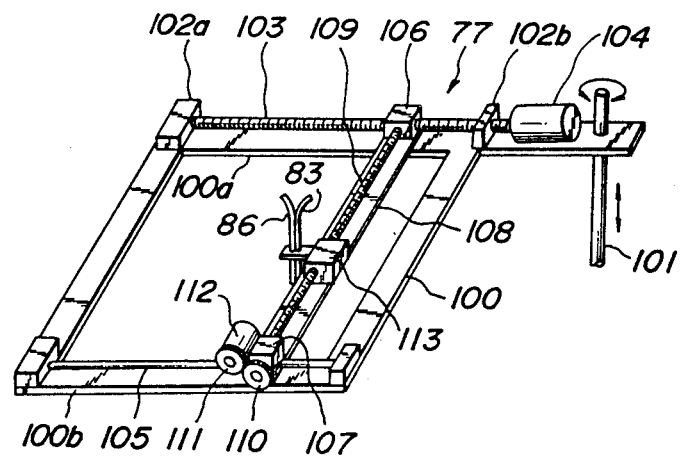
FIG. 10 is a perspective view showing delivery nozzles.

In this embodiment, as shown in FIGS. 8 to 10 in detail, a rack 88 for holding one hundred reaction vessels 87 in a matrix is successively transported between the thermostats 71 to 75 so as to effect the desired reaction. After that, the rack 88 is transported to the stage 76 and after the indicator reaction, liquid in each reaction vessels 87 is sucked into the fluorometry unit 81 so as to effect the fluorometry. To this end, hooks 89 are secured to the rack 88 and are engaged with bifurcated arm 90 so as to support the rack 88. As shown in FIG. 9, the arm 90 is secured to a shaft 93 supported by bearings 91 and 92 so as to rotate and also move in its axial direction. In the shaft 93 are formed a first gear 93a extended in the shaft direction and a second gear 93b extended in a circumferential direction. The first gear 93a is connected to a first motor 97 by means of intermediate gears 95 and 96. Therefore, a rotation of the first motor 97 makes the shaft 93 i.e. the arm 90 rotate in an arrow direction. Moreover, the second gear 93b is connected to a second motor 99 through a gear 98.

Therefore, it is possible to move the shaft 98 i.e. the arm 90 up and down by rotating the second motor 99 in both directions.

Under the condition shown in FIG. 8, the arm is positioned at the first thermostat 71 and the reaction vessels 87 supported by the rack 88 are immersed into the thermostat liquid having a temperature of $-30°$ C. If a start switch is actuated after given amounts of sample and cycling mixture are delivered into all the reaction vessels 87, the second motor 99 is energized and thus the shaft 93 is moved upward. As a result, the reaction vessels 87 are pulled up from the first thermostat 71. Then, the second motor 97 is energized and the arm 90 is rotated to a position just above the second thermostat 72. After that, the reaction vessels 87 are immersed into the thermostatic liquid in the second thermostat 72, and then the automatic cycling reaction is performed for a given time interval.

After the cycling reaction is finished, the motors 97 and 99 are energized again so as to transport the reaction vessels 87 into the third thermostat 73. Since the third thermostat 73 is maintained at about 100° C., the automatic cycling reaction is stopped. Then, the reaction vessels 87 are transported into the fourth thermostat 74, and a given amount of indicator reagent is delivered into all the reaction vessels 87.

FIG. 10 is a perspective view showing a construction of the delivery and stir device 77. In this embodiment, use is made of a rectangular frame 100 having one side 100a connected to a shaft 101 which is moved up and down and is rotated reversibly. Although not shown in FIG. 10, use may be made of various mechanisms for such up and down movement and rotational movement. To the side 100a of the frame 100 is arranged a first lead screw 103 through bearings 102a and 102b. Moreover, this first lead screw 103 is connected to a first motor 104. To a side 100b opposite to the side 100a is secured a guide rod 105 in parallel with the first lead screw 103. Further, a first nut block 106 is engaged with the first lead screw 103, and a slide block 107 is arranged slidably to the guide rod 105. Between these blocks 106 and 107 is arranged a plate 108 and is rotatably supported a second lead screw 109. To one end of the second lead screw 109 is secured a gear 110 to which a second motor 112 is connected through a gear 111. Moreover, a second nut block 113 is engaged with the second lead screw 109, and the delivery nozzle 83 and the air nozzle 84 are secured to the nut block 113. As mentioned above, the delivery nozzle 83 is connected to the indicator reagent tank 85 through the delivery pump (not shown), and the air nozzle 84 is connected to the air pump (not shown).

In the present embodiment, the delivery and stir device 77 is at first removed from a position just above the fourth thermostat 74 by rotating the shaft 101 at the uppermost position. Under such a condition, the arm 90 is rotated to transport the rack 88 just above the fourth thermostat 74. Then the arm 90 is moved downward to immerse the reaction vessels 87 into the thermostatic liquid. Next, the delivery and stir device 77 is positioned just above the rack 88 by rotating the shaft 101. Under such a condition, the first and second motors 104 and 112 are energized to position the nozzles 83 and 84 just above the predetermined reaction vessel 87. Then, the shaft 101 is moved downward to delivery and stir the indicator reagent. By repeating the operation mentioned above for successive reaction vessels 87, the predetermined amount of indicator reagent is delivered into all the reaction vessels 87. Then, the delivery and stir device 77 is pulled up from the fourth thermostat 74 by driving the shaft 101. After that, the rack 88 is transported into the fifth thermostat 75 by rotating the arm 90 again so as to effect the indicator reaction. After the predetermined indicator reaction is finished, the rack 88 is transported to the stage 76 by driving the arm 90 again. At the stage 26 is provided the suction device 78. The suction device 78 has the substantially same construction as that of the delivery and stir device 77, except that the suction device 78 has only one suction nozzle 115. The test liquid in the reaction vessel 87 can be successively supplied into the flowcell provided in the fluorometry unit 81 by suitably driving the suction device 78.

In the embodiment shown in FIGS. 7 to 10, use is made of a plurality of thermostats each maintained at the predetermined temperature and the rack for supporting a number of reaction vessels is transported between these thermostats. Therefore, it is possible to effect the rapid temperature change of the liquids contained in reaction vessels from a certain temperature to the next one, and thus the measuring accuracy can be improved. Moreover, since respective thermostats is always maintained at only one predetermined temperature, it is possible to perform the control operation of the thermostat in an easy manner. Further, in the explanation mentioned above, a washing operation of delivery nozzle, suction nozzle and flowcell provided in the fluorometer unit is omitted, but it is possible to effect the washing operation as is the same as the embodiment mentioned above.

Figure 11:
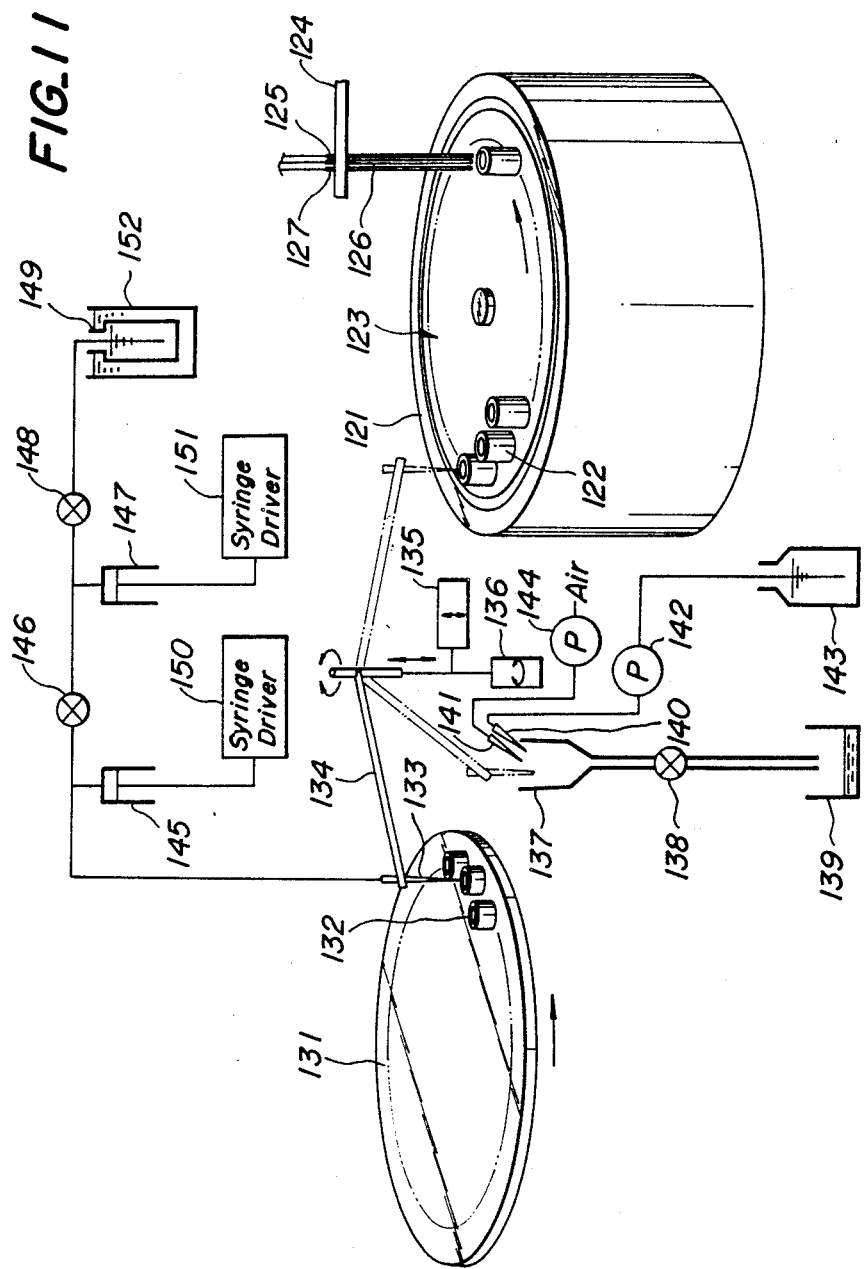
FIG. 11 is a schematic view illustrating still another embodiment of the automatic analyzing apparatus according to the invention.

FIG. 11 is a schematic view showing still another embodiment of the automatic chemical analyzer according to the invention. According to the present embodiment, the sample and the cycling mixture are automatically delivered into the reaction vessel, in the automatic chemical analyzer utilizing the automatic reaction device shown in FIGS. 1 to 6. Therefore, in this embodiment, a sampler 131 is rotated intermittently in the predetermined direction, and one hundred sample cups 132 are detachably secured on the sampler 131 equidistantly along the same circumference. In addition, a delivery nozzle 133 is movably arranged from a predetermined stop position (sample sucking position) of the sample cup 132 secured or the sampler 131 to a predetermined stop position (sample and cycling mixture discharging position) of a reaction vessel 122 supported by a turntable 123 in a reaction tank 121. The delivery nozzle 133 is supported by an arm 134, and the arm 134 is moved up and down by an arm up and down mechanism 135 and is rotated by an arm rotation mechanism 136. In this manner, the delivery, nozzle 133 is immersed in the sample contained in the sample cup 132 positioned at the sample sucking position, and is also inserted in the reaction vessel 122 positioned at the sample and cycling mixture discharging position. Moreover, a washing tank 137 is arranged under a rotation arc of the delivery nozzle 133 between the sampler 131 and the reaction tank 121, and the delivery nozzle 133 is controlled to position at the washing tank 137. In addition, at the position mentioned above, the arm 134 is moved downward so as to insert the delivery nozzle 133 into the washing tank 137. The washing tank 137 is connected to a waste liquid tank 139 through a valve 138, and further two nozzles 140 and 141 are arranged at an upper opening portion of the washing tank 137. The nozzle 140 is connected with a washing liquid tank 143 through a pump 142 so as to discharge the washing liquid into the washing tank 137, and also the nozzle 141 is connected with an air pump 144 so as to supply the air into the washing tank 137. The delivery nozzle 133 is connected with a cycling mixture tank 149 containing the cycling mixture therein through sample delivery syringe 145, valve 146, cycling mixture delivery syringe 147 and valve 148. Therefore, predetermined amounts of sample and cycling mixture can be delivered into the reaction vessel 122 by suitably operating the valves 146 and 148 and the delivery syringes 145 and 147 with the aid of syringe driving mechanisms 150 and 151. Moreover, the cycling mixture tank 149 is accommodated in a thermostat 152 to cool it by, for example, ice, and in a conduit extending from the cycling mixture tank 149 to the delivery nozzle 133 is filled with the cycling mixture.

Hereinafter, an operation of this embodiment will be explained.

First, a plurality of sample cups 132 each containing the sample therein are set to the sampler 131, and the reaction vessels 122, the number of which is the same as that of the samples, are set in the turntable 123. After that, the temperature of the antifreeze liquid in the reaction tank 121 is maintained at $-30°$ C. by actuating the apparatus. Under such a condition, the turntable 123 and the sampler 131 are rotated intermittently in a synchronous manner, and then the predetermined amount of sample contained in successive sample cups 132 in the sampler 131 is delivered into successive reaction vessels 2 together with the predetermined amount of cycling mixture.

In the delivery of sample and cycling mixture mentioned above, first of all at the sample sucking position, the arm 134 is moved downward for a predetermined distance by means of the arm up and down mechanism 135 so as to immerse the delivery nozzle 133 into the sample in the sample cup 132 positioned at the sample sucking position. Under such a condition, the valve 146 is closed and the valve 148 is opened so that the sample of 1 $\mu$l and the cycling mixture of 50 $\mu$l are respectively sucked into the sample delivery syringe 145 and the cycling mixture delivery syringe 147 with the aid of the syringe driving mechanisms 150 and 151. Then, the arm 134 is moved upward by means of the arm up and down mechanism 135 so as to pull up the delivery nozzle 133 from the sample cup 132, and is rotated for a predetermined distance by means of the arm rotation mechanism 136 so as to position the delivery nozzle 133 at the sample and cycling mixture discharging position on the turntable 123. After that, the arm 134 is moved downward by means of the arm up and down mechanism 135 so as to insert the delivery nozzle 133 into the reaction vessel 122 positioned at the discharging position. Under such a condition, the valve 146 is opened and the valve 148 is closed, so that predetermined amounts of sample and cycling mixture are respectively sucked into the delivery syringes 145 and 147 with the aid of the syringe driving mechanisms 150 and 151. Then, the arm 134 is moved upward by means of the arm up and down mechanism 135 so as to pull up the delivery nozzle 133 from the reaction vessel 122, and is rotated for a predetermined distance by means of the arm rotation mechanism 136 so as to position the delivery nozzle 133 above the washing tank 137. After than, the arm 134 is moved downward by means of the arm up and down mechanism 135 so as to insert the delivery nozzle 133 into the washing tank 137. Then, the valve 138 is closed and a predetermined amount of washing liquid is delivered into the washing tank 137 through the nozzle 140 by actuating the pump 142. Under this condition, at least a portion of the delivery nozzle 133 to be immersed into the sample contained in the sample cup 132 is immersed into the washing liquid so as to effect the washing operation thereof. After that, the valve 138 is opened to discharge the washing liquid in the washing tank 137 into the waste liquid tank 139, and the air is supplied from the nozzle 141 by actuating the air pump 144 so as to remove the washing liquid adhered to the outer portion of the delivery nozzle 133. Then, the arm 134 is moved upward and is rotated by means of the arm up and down mechanism 135 and the arm rotation mechanism 134 so as to position the delivery nozzle 133 at the predetermined sample sucking position on the sampler 131. By repeating the operation mentioned above, the predetermined amount of sample in successive sample cups 132 on the sampler 131 can be delivered into successive reaction vessels 122 on the turntable 123 together with the predetermined amount of cycling mixture without causing the contamination.

After the delivery of all the sample and cycling mixture, the number of which is previously set, is finished, the temperature of the antifreeze liquid in the reaction tank 121 is immediately increased to 25° C., and then the sample to be measured is detected and quantitized by effecting the same operations as those shown in FIGS. 1 to 6 by means of nozzles 125 to 127 secured to an arm 124.

In the present embodiment, all the operations from the delivery of sample to the detection and quantitation of the sample to be measured can be automatically performed, and thus it is very advantageous for the elimination of labor.

As mentioned above, according to the invention, it is possible to realize the automatic cycling reaction apparatus which can effect the enzymatic cycling method in an easy manner and can always obtain the highly reliable and accurate analytic result. Moreover, it is possible to realize the automatic chemical analyzer which can automatically analyze the sample to be measured in a highly accurate manner by the enzymatic cycling method with the aid of the automatic cycling reaction apparatus.

What is claimed is:

1. An automatic enzymatic cycling reaction apparatus comprising;
   first means including a turntable for supporting a plurality of reaction vessels along its periphery, each of said vessels containing given amounts of a sample and a cycling mixture including enzymes; and
   second means for holding liquids contained in the reaction vessels at a low temperature at which the enzymatic cycling reaction does not substantially occur, bringing simultaneously liquids contained in all the reaction vessels at a given cycling reaction temperature, keeping the liquids at said temperature for a given period, holding all the liquids simultaneously at a first temperature at which a cycling reaction is stopped due to loss of activity of enzymes, and then keeping all the liquids simultaneously at a second temperature lower than the first temperature, said second means comprising a reaction tank in which said turntable is arranged, means for circulating a thermostatic liquid through said tank and means for controlling the temperature of said thermostatic liquid.

2. An apparatus according to claim 1, wherein said device for controlling the temperature of the thermostatic liquid comprises a heater and a refrigerator and a switching valve for selectively passing the thermostatic liquid through the heater or refrigerator.

3. An apparatus according to claim 2, wherein said second means further comprises a lid removably placed on the reaction tank.

4. An automatic analyzer using an enzymatic cycling reaction comprising;
   first means including a turntable for supporting a number of reaction vessels along its periphery each of said vessels containing given amounts of a sample and a cycling mixture including enzymes;
   second means for keeping liquids contained in the reaction vessels at a low temperature at which the enzymatic cycling reaction does not substantially occur bringing simultaneously liquids contained in all the reaction vessels at a first temperature at which an enzymatic cycling reaction proceeds, keeping the liquids at said temperature for a given period, holding all the liquids simultaneously at a second temperature at which the enzymatic cycling reaction is stopped due to a loss of activity of the enzymes, and keeping all the liquids simultaneously at a third temperature lower than the second temperature and at which temperature an indicator reaction proceeds;
   third means for delivering a given amount of an indicator reagent into respective reaction vessels after the enzymatic cycling reaction of the liquids in the reaction vessels has been stopped; and
   fourth means for measuring fluorescent light emitted from substances produced by the indicator reaction, said second means comprising a reaction tank in which said turntable is arranged, means for circulating a thermostatic liquid through said reaction tank, and means for controlling the temperature of said thermostatic liquid.

5. An analyzer according to claim 4, wherein said temperature controlling device comprises a heater, a refrigerator and a switching valve for selectively passing the thermostatic liquid through the heater or refrigerator.

6. An analyzer, according to claim 5, wherein said second means further comprises a lid removably placed on the reaction tank.

* * * * *